US010618056B2

(12) United States Patent
Bhakdi et al.

(10) Patent No.: US 10,618,056 B2
(45) Date of Patent: Apr. 14, 2020

(54) SYSTEMS AND METHODS FOR HIGH GRADIENT MAGNETIC SEPARATION OF BIOLOGICAL MATERIAL

(71) Applicants: Sebastian Chakrit Bhakdi, Marburg (DE); Prida Malasit, Bangkok (TH)

(72) Inventors: Sebastian Chakrit Bhakdi, Marburg (DE); Prida Malasit, Bangkok (TH)

(73) Assignee: X-Zell Inc., Sunnyvale, CA (US)

( * ) Notice: Subject to any disclaimer, the term of this patent is extended or adjusted under 35 U.S.C. 154(b) by 190 days.

(21) Appl. No.: 15/137,334

(22) Filed: Apr. 25, 2016

(65) Prior Publication Data

US 2016/0236204 A1    Aug. 18, 2016

Related U.S. Application Data

(63) Continuation of application No. 12/733,594, filed as application No. PCT/EP2008/061170 on Aug. 26, 2008, now abandoned.

(30) Foreign Application Priority Data

Sep. 11, 2007    (DE) ................ 10 2007 043 281

(51) Int. Cl.
| | | |
|---|---|---|
| B03C 1/00 | (2006.01) | |
| B03C 1/28 | (2006.01) | |
| C12N 13/00 | (2006.01) | |
| B03C 1/01 | (2006.01) | |
| B03C 1/034 | (2006.01) | |
| B03C 1/032 | (2006.01) | |
| B03C 1/033 | (2006.01) | |

(52) U.S. Cl.
CPC ............ B03C 1/002 (2013.01); B03C 1/01 (2013.01); B03C 1/032 (2013.01); B03C 1/034 (2013.01); B03C 1/0335 (2013.01); B03C 1/288 (2013.01); C12N 13/00 (2013.01); B03C 2201/18 (2013.01); B03C 2201/26 (2013.01)

(58) Field of Classification Search
None
See application file for complete search history.

(56) References Cited

U.S. PATENT DOCUMENTS

| | | | |
|---|---|---|---|
| 3,826,365 A | | 7/1974 | Mercade |
| 3,983,033 A | | 9/1976 | De Latour |
| 4,664,796 A | | 5/1987 | Graham et al. |
| 5,093,474 A | | 3/1992 | Grossman et al. |
| 5,200,084 A | | 4/1993 | Liberti et al. |
| 5,391,272 A | * | 2/1995 | O'Daly ............... C12Q 1/005 204/403.1 |
| 5,466,574 A | * | 11/1995 | Liberti ............... A23L 3/32 209/214 |
| 5,512,332 A | | 4/1996 | Liberti et al. |
| 5,536,644 A | | 7/1996 | Ullman et al. |
| 5,543,289 A | | 8/1996 | Miltenyi |
| 6,013,188 A | | 1/2000 | Terstappen et al. |
| 6,602,422 B1 | | 8/2003 | Miltenyi et al. |
| 2003/0190760 A1 | | 10/2003 | Watkins et al. |

FOREIGN PATENT DOCUMENTS

| | | |
|---|---|---|
| CA | 2431683 | 12/2004 |
| CA | 2532012 | 3/2005 |
| CA | 2488955 | 6/2005 |
| CA | 2547353 | 7/2005 |
| CA | 2554138 | 8/2005 |
| CA | 2554524 | 8/2005 |
| CA | 2558018 | 10/2005 |
| DE | 19516323 | 11/1996 |
| EP | 0176113 | 4/1986 |
| WO | 2006119308 | 11/2006 |

OTHER PUBLICATIONS

Miltenyi et al., High Gradient Magnetic Cell Separation with MACS, Wiley-Liss, Inc., Cytometry, 1990, p. 231-238, vol. 11.
Sigma-Aldrich, Getatin Product Information Sheet.
Tagawa et al., Purification and Partial Characterization of the Major Outer Membrane Protein of Haemophilus somnus, American Society for Microbiology, Infection and Immunity, 1993, p. 91-96, vol. 61, issue 1.
Kadonaga et al., Affinity purification of sequence-specific DNA binding proteins, Proceedings of the National Academy of Science, Biochemistry, p. 5889-5893, vol. 83.
Fagain et al., Gel-Filtration Chromatography, Springer Science+ Business Media LLC, Methods in Molecular Biology, 2011, p. 25-33, vol. 681.
McNeill et al., Anti-phospholipid antibodies are directed against a complex antigen that includes a lipid-binding inhibitor of coagulation: B2-Glycoprotein I (apolipoprotein H), Proceedings of the National Academy of Sciences, Medical Sciences, 1990, p. 4120-4124, vol. 87.
Felix et al., Characterization and correlation analysis of pharmaceutical gelatin, Graduate School Theses and Dissertations, University of South Florida, 2003.
Reffle et al., Critical Capture Radius in Single Wire HGMS, Applied Physics, 1981, p. 225-228, vol. 24, issue 3.
International Search Report of PCT/EP2008/061170, dated May 4, 2009.
Paul et al., article entitled "Methods and Devices, Separation of Malaria-Infected Erythrocytes from Whole Blood: Use of a Selective High-Gradient Magnetic Separation Technique," The Lancet, Jul. 11, 1981.

* cited by examiner

Primary Examiner — Nghi V Nguyen
(74) Attorney, Agent, or Firm — Aurora Consulting LLC; Ashley Sloat

(57) ABSTRACT

Described herein are methods for purification of biological material using high gradient magnetic separation. For example, a method includes: providing a ferromagnetic matrix surrounded by a separation column, the separation column including an elongate body defining a lumen having an inlet and an outlet; applying an external magnetic field to the separation column; saturating unspecific binding sites in the ferromagnetic matrix by applying a buffer solution to the ferromagnetic matrix; and introducing biological material into the lumen of the separation column. In some embodiments, the ferromagnetic matrix is uncoated, and the buffer solution includes at least one macromolecule. In some embodiments, the method further includes incubating the ferromagnetic matrix with the buffer solution for at least three minutes to equilibrate the ferromagnetic matrix.

18 Claims, 3 Drawing Sheets

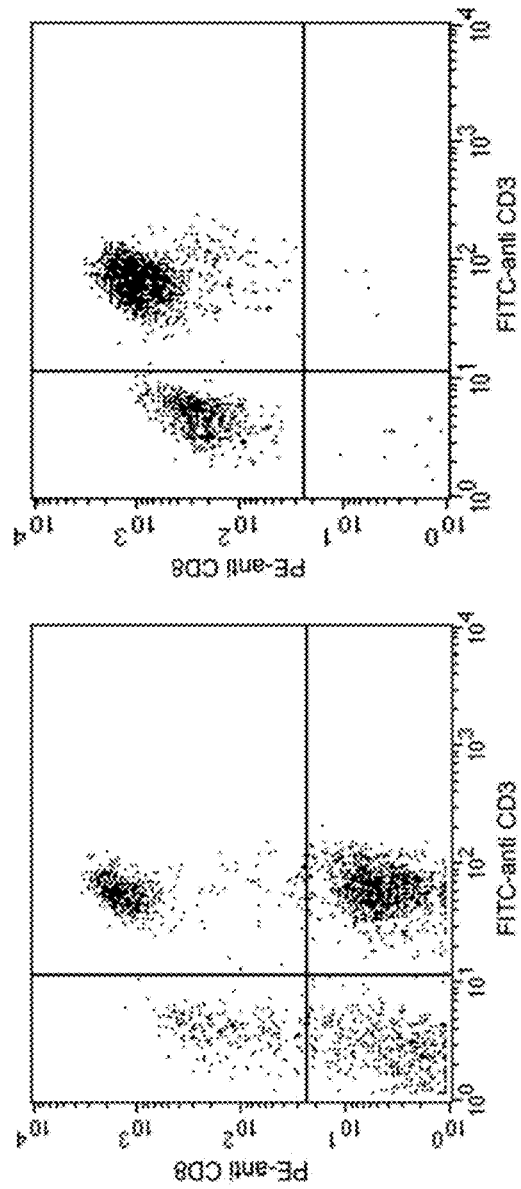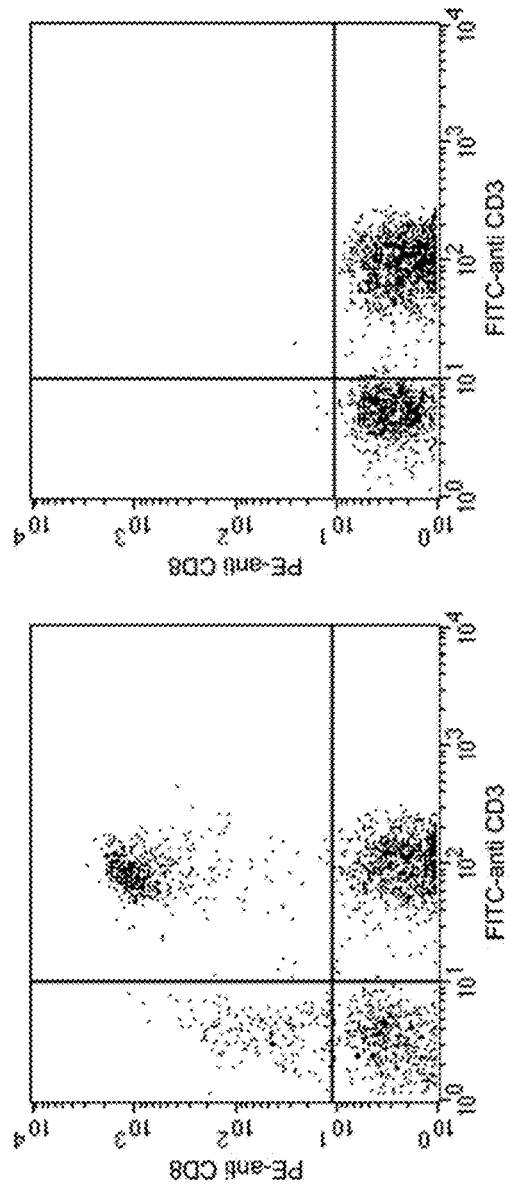

SYSTEMS AND METHODS FOR HIGH GRADIENT MAGNETIC SEPARATION OF BIOLOGICAL MATERIAL

CROSS-REFERENCE TO RELATED APPLICATIONS

This patent application claims priority as a continuation of U.S. patent application Ser. No. 12/733,594, filed on Mar. 10, 2010, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

FIELD OF THE INVENTION

This invention relates generally to the field of molecular biology, and more specifically to new and useful systems and methods for high gradient magnetic separation of biological material.

BACKGROUND

The invention concerns a method for high gradient magnetic separation (HGMS) technology for the separation and purification of biological material.

The separation and purification of certain particles from heterogeneous particle suspensions is of great importance for a variety of analytic methods especially in the field of biomedical research. Generally, particles to be purified, called "target particles" in the following, frequently differ only minimally from the rest of the particles contained in the suspension, called "non-target particles" in the following. Target particles and non-target particles are often cells or cell fragments, however, they can be any other biological substances.

Some established separation methods use magnetic properties of target particles, where the target particles have naturally occurring "intrinsic" magnetic properties, or where the target particles are labeled through targeted attachment of synthetic magnetic particles before the actual separation procedure Intrinsically magnetic particles, for example, are red blood cells, given that the hemoglobin contained in them exists in the de-oxygenated or oxidized, but not in the oxygenated state. Here, de-oxygenated means not oxygen carrying and oxygenated means oxygen carrying. In the latter case, the hemoglobin molecule carries an oxygen molecule with non-covalent binding (i.e., reversible binding). The oxidized state of hemoglobin has to be differentiated, in which the oxygen atoms or other oxidizing atoms are bound covalently (i.e., non-reversibly) to the central iron atom of the hemoglobin molecule.

Now the orbitals of the central iron atom contained in the hemoglobin molecule carry unpaired electrons both in the de-oxygenated as well as the oxidized form (but not in the oxygenated form). The unpaired spin of these electrons enables the induction of magnetic poles in the iron atom by application of a magnetic field.

A magnetic field of the conventional kind, however, does not exert a directed net magnetic force on a particle which contains such iron atoms, since, due to the very small atomic diameter, attracting and repelling forces at the North Pole and South Pole of the polarized iron atoms keep the balance. Also, the particle will lose its polarization after removal of the magnetic field. This kind of magnetism is known as "paramagnetism." A special form of paramagnetism is sometimes called "superparamagnetism." Between both these forms, however, physically no clear separation exists, therefore, in the following, the terms "paramagnetism" and "paramagnetic" shall encompass the terms "superparamagnetism" and "superparamagnetic."

Also, the well-established synthetic secondary particles used for magnetic labeling of target particles are paramagnetic and usually contain, very similar to oxidized hemoglobin, small amounts of oxidized iron or another magnetizable substance. Moreover, they are ideally so small that they form stable colloids in suspension, in other words, they do not sediment over long periods of time (months to years); therefore, their diameter in general measures 30-200 nm. Commercially available particles of this kind are distributed alone or conjugated to antibodies, for example by chemicell GmbH (Eresburgstrasse 22-23, D-12103 Berlin, Germany), micromod Partikeltechnologie GmbH (Friedrich-Barnewitz-Str.4, D-18119 Rostock, Germany), or Miltenyi Biotech GmbH (Friedrich Ebert Straүe 68, D-51429 Bergisch Gladbach, Germany).

An established method to purify paramagnetic particles, in other words, to separate paramagnetic particles from particle suspensions, is the creation of extremely high magnetic field gradients. A sufficiently high magnetic gradient leads to the fact that north and south poles of the paramagnetic particles experience a difference in attracting and repelling forces and therefore, a directed net-magnetic force. This technology is known under the term high gradient magnetic separation (HGMS).

Here a distinction is to be made between so-called "internal" and "external" high gradient magnetic separators. First descriptions of the HGMS-technology referred to internal separators. These can be found in Oberteuffer (IEEE Transactions on Magnetics, Mag-9, No. 3, September 1973:303-306) and in the U.S. Pat. No. 3,676,337. A ferromagnetic material in a suitable, non-magnetic container which serves as separation chamber, is introduced into a strong homogenous magnetic field which can be generated by an electromagnet or by a horseshoe shaped permanent magnet (dipole magnet). In this case, the ferromagnetic material generally carries the name "matrix;" it can be of filamentary (wire-like or thread-like), of spherical (ball-like) or of an otherwise different shape, for example it can consist of punched sheet steel. The ferromagnetic material of the matrix experiences a magnetization corresponding to its magnetic susceptibility X through the externally applied field. Commencing from the surface of the matrix material, magnetic field gradients are created which can reach over 100 Tesla per centimeter; whereby the magnitude of the gradient is in the inverse ratio to the diameter of the utilized filamentary or spherical elements. "External" high gradient magnetic separators reach similarly high gradients through a technically more complex, special arrangement of the magnets outside the actual separation chamber, as for example disclosed in WO 98/055236, WO 99/019071 or U.S. Pat. No. 6,241,894 B1. As a fundamental difference, the need for a matrix inside the separation chamber does not arise here.

Nowadays, internal high gradient magnetic separators are the most widely used in biomedical research. U.S. Pat. Nos. 4,664,796 and 5,200,084 describe particular embodiments of such separators.

U.S. Pat. No. 5,200,084 discloses an apparatus and a method that is particularly directed at the purification of small amounts of biological material in the wells of a microtiter plate. Among others, purifications of up to 83% of CD4 cells labeled with paramagnetic secondary particles from peripheral mononuclear blood cells (PBMCs) are reported.

To the inventor's knowledge, at present only one technical design of an internal high gradient magnetic separator achieves high purification rates, as disclosed in the WO 96/26782 and the EP 0942766 B1. To avoid unspecific binding of non-target particles to the matrix, which impair the purification result in the named documents, the separation chamber of said separator contains a polymer-coated matrix. The polymer is drawn onto the matrix in several steps, as described in detail in the WO 96/26782. According to the information given by the authors, the so assembled separation chamber distinguishes itself by the fact that the polymer creates a hard, closed, liquid impermeable and ion impermeable coating containing less than 1% water on the ferromagnetic material of the matrix; and that the polymer-coated matrix fills 60-70% of the total volume of the described separation chamber.

According to the named publication, apart from decreasing unspecific binding of non-target particles to the matrix, said coating is supposed to also avoid damage of the biological material to be separated by direct contact with the ferromagnetic matrix material (e.g., physical damage), as well as to exclude a chemical reaction of the ferromagnetic matrix material with the buffer solution used for suspension of the biological material, since freed ions could also lead to damage of the biological material to be separated (e.g., chemical damage). Both of these kinds of damage, however, are to be considered hypothetical, since no scientifically secured findings are available. Moreover, Paul et al. conversely reported no impairment of morphology and viability of blood cells and blood cell fragments that passed a non-treated stainless steel matrix of a HGMS-column (Paul et al. Clinical and Laboratory Haematology, 7, 1985:43-53.

All patents and publications mentioned up to this point are included herein by reference.

The kind of separation chambers described are costly due to their time intensive production process particularly for the coating of the matrix. They are commercially available from Miltenyi Biotech GmbH (loc.cit.).

They achieve high purifications especially when used for particles labeled with synthetic paramagnetic particles from particle suspensions.

The application of said separation chambers with a coated matrix for intrinsically (naturally) paramagnetic particles was investigated. Here, malaria-infected red blood cells served as intrinsically paramagnetic particles. The pathogens of malaria, parasites of the genus *Plasmodium* from the group of the protozoa, selectively attack red blood cells and have the property to oxidize the central iron atom of the free heme molecule arising in the infected red blood cell into trivalent iron. This is, as described above, paramagnetic. Therefore, malaria infected red blood cells should be separable from non-infected and oxygenized red blood cells in separation chambers of high gradient magnetic separators. This was shown first in 1981 by Paul et al. (Lancet, Jul. 11, 1981:70-71) in 1981. At present, the described, commercially available separation chambers with coated matrix are said to achieve purifications of over 80% (Uhlemann et al., MACS&more 2000; 4 (2):7-8, Trang et al., Malaria Journal 2004; 3:1-7).

The specified investigations, however, refer to only one of the total four known pathogenic malaria pathogens in humans, namely *Plasmodium falciparum*, the pathogenic agent of Malaria tropica, as well as one other malaria pathogen in rodents, *Plasmodium berghei*. Further scientific studies about the total nearly 120 further known *Plasmodium* species are not available. It is known to the inventors, however, that the application of the commercially available separation chambers to the purification of red blood cells infected with *Plasmodium vivax*, the pathogen of Malaria tertiana also occurring in humans, does not always lead to satisfactory results.

From the forgoing explanations it is obvious that further improvements of the purification effectiveness of the HGMS technology would be of great usefulness for the field of biomedical research. This also applies with reference to the cost efficiency, since the known sophisticated separation chambers are not always available in different areas simply for cost considerations, particularly, in the investigation of malaria pathogens, which particularly affects countries with smaller medical and research budgets. Therefore, it is the task of the invention to provide a HGMS separation column that achieves better purification results in a cost-efficient way.

SUMMARY

Various aspects of the present disclosure are directed to systems and methods for high gradient magnetic separation of biological material. On aspect of the disclosure is directed to a method for purification of biological material using high gradient magnetic separation. In various embodiments, the method includes: providing a ferromagnetic matrix surrounded by a separation column, the separation column including an elongate body defining a lumen having an inlet and an outlet; applying an external magnetic field to the separation column; saturating unspecific binding sites in the ferromagnetic matrix by applying a buffer solution to the ferromagnetic matrix; and introducing biological material into the lumen of the separation column.

In some embodiments, the ferromagnetic matrix is uncoated.

In some embodiments, the buffer solution comprises at least one macromolecule. In some such embodiments, the macromolecule in the buffer solution is a globular protein or a filamentous protein. Further, in some such embodiments, the globular protein is bovine serum albumin and the filamentous protein is gelatin. In some embodiments, the macromolecule constitutes 3%-7% of the buffer solution.

In some embodiments, the biological material is suspended in the buffer solution. In some such embodiments, applying the buffer solution introduces the biological material.

In some embodiments, a target subset of the biological material couples to the ferromagnetic matrix when the external magnetic field is applied. In some such embodiments, applying the external magnetic field includes applying a permanent magnet and/or an electromagnet. Further, in some such embodiments, the target subset of the biological material is intrinsically magnetic and/or magnetically labeled.

In some embodiments, the method further includes removing the external magnetic field to allow the target subset of biological material to be removed from the ferromagnetic matrix. In some such embodiments, the external magnetic field is removed by spatial separation and/or turning off power to the external magnetic field.

In some embodiments, the method further includes removing the non-target subset of the biological material by washing the ferromagnetic matrix with the buffer solution.

In some embodiments, the method further includes continuously covering the ferromagnetic matrix with the buffer solution to maintain saturation of the unspecific binding sites.

In some embodiments, the biological material is one of cells, cell aggregates, or cell parts.

In some embodiments, the method further includes providing a storage container for coupling to the separation column. In some such embodiments, the storage container introduces the buffer solution into the inlet of the separation column through an adjustable flow velocity device.

In some embodiments, the separation column further includes an adjustable flow velocity device coupled to the outlet of the separation column.

In some embodiments, the ferromagnetic matrix includes wire-like interlaced filaments, thread-like interlaced filaments, spherical ferromagnetic elements, a ferromagnetic metallic sheet having punched-through holes, and/or a ferromagnetic metallic plate having punched-through holes.

In some embodiments, the buffer solution has a density which matches the density of the biologic material to be purified such that the particles are suspended in the buffer solution.

In some embodiments, the buffer solution has a high viscosity resulting in a laminar flow through the separation column.

Another aspect of the disclosure is directed to a method for separation of a target subset of biological material from a non-target subset of biological material using high gradient magnetic separation. In various embodiments, the method includes: providing a ferromagnetic matrix surrounded by a separation column, positioning the separation column in an external magnetic field; and applying a buffer solution to the ferromagnetic matrix to saturate unspecific binding sites in the ferromagnetic matrix; and applying biological material to the ferromagnetic matrix.

In some embodiments, the method further includes incubating the ferromagnetic matrix with the buffer solution for at least three minutes to equilibrate the ferromagnetic matrix.

Another aspect of the disclosure is directed to a method for the separation or purification of intrinsically magnetic or preparatively magnetically labeled biological material by means of high gradient magnetic separation. In some embodiments, the suspension with the biological material flows through a ferromagnetic matrix arranged in an external magnetic field so that the material adheres to the matrix. In some such embodiments, the matrix is uncoated and the biological material is suspended in a buffer solution with a base solution and macromolecules which saturate unspecific binding sites of the matrix during flow-through the matrix.

In some embodiments, the matrix and a separation column surrounding it is equilibrated before through flow of the suspension by a pre-incubation with pure buffer solutions (i.e., buffer solution containing no biological material), and indeed over a sufficiently long period of time to saturate unspecific binding sites in the matrix, particularly over a duration of about 3 to about 20 or about 5 to about 10 minutes. In some such embodiments, the matrix is always kept covered by the buffer solution during equilibration.

In some embodiments, the unwanted biological material leaves the separation column as the eluate, (i.e., a liquid leaving the matrix is captured after the through flow). In some such embodiments, after introduction of the suspension into the matrix, additional pure buffer solution is flowed through the matrix, with the magnetic field still activated until it is ensured that the suspension has completely left the matrix. Further, in some such embodiments, the matrix is always kept covered by the buffer solution during the through flow.

In some embodiments, for the separation of wanted biological material, after introduction of the suspension into the matrix with still activated magnetic field, additional pure buffer solution is flowed through the matrix until it is ensured that the suspension has completely left the matrix, and subsequently the matrix is washed with additional pure buffer solution with the external magnetic field deactivated by spatial separation or switch-off. In some such embodiments, the eluate is captured, with the matrix always kept covered by the buffer solution during the entire process.

In some embodiments, the captured eluate is centrifuged and the method is repeated with the centrifuged biological material without the liquid phase of the eluate one or several times.

Another aspect of the disclosure is directed to a high gradient magnetic separation apparatus for the separation or purification of magnetic or magnetically labeled biological material. In various embodiments, the system includes a magnet, a separation column, and a ferromagnetic matrix arrangeable in an inner space of the separation column. In some embodiments, the system further includes a storage container containing a buffer solution for the equilibration of the separation column and/or for the suspension of the biological material. In some such embodiments, during operation, a magnetic field generated by the magnet can generate a high gradient magnetic field in the matrix and buffer solution can flow through the separation column from the liquid storage container. In some embodiments, the buffer solution encompasses a base solution and macromolecules, which are able to saturate unspecific binding sites of the matrix.

In some embodiments, the buffer solution has a density which matches the density of the particles of the biological material to be separated so far that a force due to gravity acting on the particles is largely compensated and therefore, the particles are almost suspended in the buffer solution.

In some embodiments, the buffer solution has a high viscosity which facilitates a laminar flow through the separation column with a flow velocity suitable for the separation process.

In some embodiments, the magnet is a permanent magnet or an electromagnet which is shaped so that the separation column can be arranged in the particularly homogenous magnetic field generated by it. In some such embodiments, the separation column can selectively stand under the influence of the magnetic field or not by spatial separation and/or by switching it off.

In some embodiments, the matrix is uncoated and/or has ordered or non-ordered filamentary, spherical or differently shaped material, in particular stainless, magnetic steel or steel wool.

In some embodiments, the liquid storage container is connected to the separation column so that buffer solution can be introduced into the separation column via a flow limitation device with an adjustable flow velocity or not. In some embodiments, the separation column has a flow limitation device which can influence the outflow out of, and the flow velocity inside the separation column.

In some embodiments, the ionic strength of the base solution is adapted in dependence on the macromolecules so that aggregating effects of the macromolecules on the biological material are compensated. In some such embodiments, the base solution has an isoosmolar concentration of the cations: sodium, potassium, magnesium, and/or calcium and of the anions: chloride, phosphate, sulfate, and/or carbonate, and is, in particular, a phosphate buffered saline or sucrose solution or a mixture thereof.

In some embodiments, the macromolecules include natural or synthetic polyelectrolytes or polyampholytes, particularly synthetic polyelectrolyte or organic polyelectrolyte d-glucoronic acid. In some embodiments, the macromolecules have an isoelectric point which leads, at the pH value of the base solution, to a charge which corresponds to the charge of the particles of the biological material to be separated. In some embodiments, the macromolecules have a molecular weight of about 10,000 to about 100,000 kDa, particularly from about 30,000 to about 70,000 kDa.

In some embodiments, the macromolecules include globular proteins, particularly albumins, bovine or human serumalbumin, ovoalbumin, lactoalbumin or plant albumins, β-lactoglobulin, κ-casein, histones, protamines, globulines, prolamines or glutelines with a concentration of about 3% to about 7%, particularly about 4% to about 5% in relation to the buffer solution.

In some embodiments, the macromolecules include filamentary proteins, in particular hydrolysed collagens in a concentration of about 0.3 to about 20 wt-%, particularly of about 1 to about 10 wt-%, or gelatins, bovine gelatins, porcine gelatins or teleosteangelatins in a concentration of about 0.3% to about 1.5%, particularly from about 0.4% to about 0.8%, which have a low gel strength of about 150 Bloom or less, particularly of about 75 Bloom or less.

BRIEF DESCRIPTION OF THE DRAWINGS

FIG. 4A shows a flow cytometric analysis of a third example as a scatter plot. The scatter plot illustrates the proportion of CD8 positive blood cells in a suspension of peripheral mononuclear cells (PBMCs) before purification. An isoosmolar phosphate buffered sucrose solution with 0.75% gelatin as buffer solution as in the first example;

FIG. 4B shows a flow cytometric analysis of a third example as scatter plot. The scatter plot illustrates the eluate from the separation column after passage of PBMCs, and washing and removal of the separation column from the magnetic field. An isoosmolar phosphate buffered sucrose solution with 0.75% gelatin as buffer solution as in the first example;

FIG. 5A shows a representation according to FIG. 4A of a fourth example, but using bovine serum albumin (BSA) containing phosphate buffered saline solution (PBS) as buffer solution as in the second example; and FIG. 5B shows a representation according to FIG. 4B of a fourth example, but using bovine serum albumin (BSA) containing phosphate buffered saline solution (PBS) as buffer solution as in the second example.

DETAILED DESCRIPTION

Figure 1:
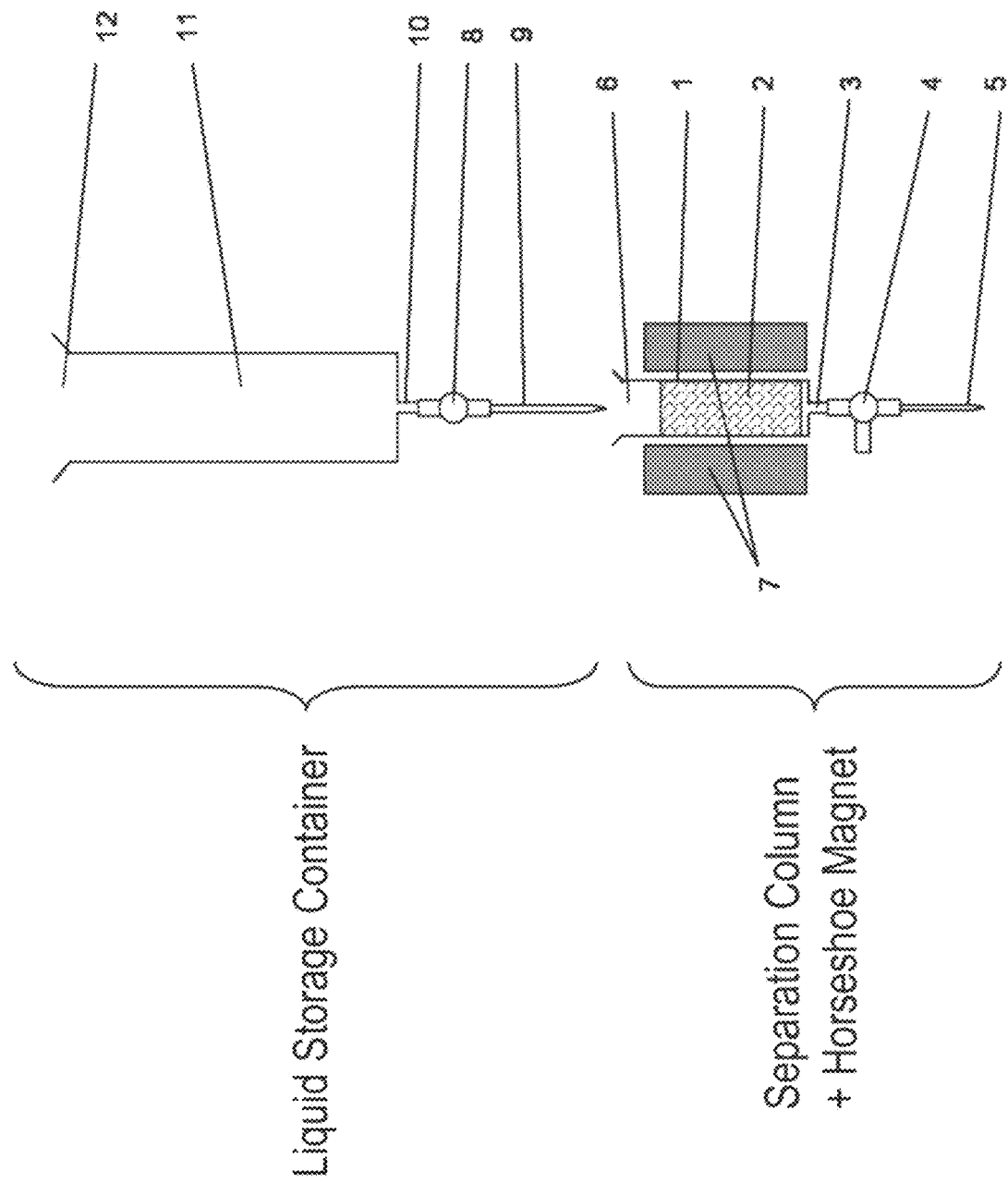
FIG. 1 illustrates a schematic front view of the assembly of an embodiment of the HGMS apparatus according to the present invention and the separation column.

The following description of the preferred embodiments of the invention is not intended to limit the invention to these preferred embodiments, but rather to enable any person skilled in the art to make and use this invention. Disclosed herein are systems and methods for high gradient magnetic separation of biological material.

The solution according to the present invention relies on the principle of solving the problem of unspecific binding of non-target particles to the matrix of the HGMS separation column through a buffer solution, with the properties stated in the claims, for the equilibration of the separation column, and for the suspension of the biological material to be separated. The complicated and cost-driving coating can then be dispensed with because the unspecific binding sites of the separation column are saturated by the buffer solution. The unspecific binding sites are to be understood as those at which particles attach independently of the magnetic properties, thus the particles would bind mechanically, electrically, chemically, physically or still differently. Thereby, non-target particles would be selected independently of the magnetic gradient, which would lead to incomplete purification or separation results. The biological material is preferably cells, cell aggregates or cell parts, which possess intrinsic paramagnetic properties, or which can be directly or indirectly marked by means of paramagnetic or superparamagnetic particles.

The solution according to the present invention has the advantage that the buffer solution can be provided relatively simply and cost efficiently. Time, material, and cost consuming pre-treatment of the separation column and the matrix contained in it can be reduced. This simplification has the advantage of improved purification results compared with conventional separation columns with their sophisticated coatings of the matrix.

The buffer solution preferably has a density which matches the density of the particles of the biological material to be separated to an extent so large, that a gravitational force acting on the particles is essentially compensated and therefore the particles almost float in the buffer solution, and/or the buffer solution has a high viscosity, which enables a laminar flow through the separation column with a flow velocity suitable for the separation process. In this way the target particles can be kept so long in the range of action of the high gradient magnetic field without the disturbing influence of gravitational force that they precipitate out to a very high degree. Thus a particularly high degree of separation and purification is obtained.

Advantageously, the magnet is a permanent or electromagnet which is shaped so that the separation column can be arranged within the particularly homogenous magnetic field generated by it, and the separation column can optionally stand under the influence of the magnetic field or not by spatial separation and/or switch-off. By adjustment of the shape, the magnetic field can be brought close to the matrix and therefore provides a sufficient external magnetic field strength. Moreover, the magnet has to be sufficiently strong so that by focusing of the field strength via the matrix, a strong high gradient magnetic field can be generated. By spatial separation or switch-off, the target particles can be selectively held and freed, depending on whether the liquid that flows out of the separation column is supposed to contain the target particles in the particular working step or not.

Preferably, the matrix is non-coated and/or has ordered or non-ordered, filamentary, spherical or otherwise shaped material, particularly non-rusting, magnetic stainless steel or steel wool. A non-coated matrix is especially cost-efficient, and a coating is not necessary according to the present invention. Alternatively, it could be imagined, however, that a coating is provided, and this coating could then be non-complete or less high-grade than customary. The relatively wide-meshed arrangement of the matrix prevents a physical or chemical damage of the biological material to be separated, for example damage to sensitive cells could be avoided effectively in the experiments described below.

Preferably, the storage container is connected to the separation column, so that buffer solution can be introduced into the separation column with an adjustable flow velocity via an inflow limitation device or not, and/or the separation column has a through flow limitation device, which is able to control the outflow form and the flow velocity inside the separation column. Here the connection between storage container and separation column can be provided as a technical construction, possibly via a tube, but also by free dripping. Thus, the flow velocity can be adapted to the biological material, to the buffer solution, and to the particular work step. A complete blocking of the inflow of buffer solution is also made possible, for instance to allow a phase of rest for equilibration of the separation column, or in work steps in which no buffer solution is required.

The buffer solution includes a base solution and at least one macromolecule. For example, the buffer solution includes from 80 to 99.8 wt % base solution and from 0.2 to 20 wt % macromolecules.

Preferably, the buffer solution has a base solution, whose ionic strength is adapted in dependence on the macromolecules so that aggregating effects of the macromolecules on the biological material are compensated. The base solution has an isoosmolar concentration of the cations sodium, potassium, magnesium or calcium and of the anions chloride, phosphate, sulphate or carbonate, in particular it is a phosphate buffered saline or sucrose solution or a mixture thereof. The base solution should also be matched in its properties like pH-value and others to both the biological material and the macromolecules for saturation of the unspecific binding sites, to achieve even better results according to the mechanism described elsewhere herein. Unwanted aggregations of the biological material are prevented especially well if the isoosmolar (physiologic) phosphate buffered saline solution is replaced by isoosmolar phosphate buffered sucrose solution completely or partly. Other sugar solutions than sucrose solutions are also conceivable.

For example, the buffer solution includes 0.2 to 10 wt % gelatin, 9.5-10 wt %/sucrose, 80-95 wt % distilled water and sodium phosphate for buffering; and/or 3-10 wt % bovine serum albumin, 0.85-0.95 wt % saline and 89-98 wt % distilled water, and sodium phosphate for buffering; and/or 0.5-20 wt % hydrolyzed collagen, 5-10 wt % sucrose, 0.1-0.9 wt % saline and sodium phosphate for buffering.

Advantageously, the macromolecules may encompass natural or synthetic polyelectrolytes or polyampholytes which may be strong or weak, particularly the synthetical polyelectrolyte Orotan 1850 or the organic polyclectrolyte D-glucoronic acid, and/or the macromolecules have an isoelectric point which leads at the pH-value of the base solution to a charge which corresponds to the charge of the particles of the biological material to be separated and/or the macromolecules have a molecular weight from 10,000 to 100,000 kDa, particularly from 30,000 to 70,000 kDa. Such buffer solutions lead to especially good purification results.

Furthermore, the macromolecules may encompass preferably globular proteins, particularly albumins, bovine or human serum albumin, ovoalbumin, lactoalbumin or plant albumins, β-lactoglobulin, κ-casein, histones, protamines, globulines, prolamines or glutelines with a concentration from 3 to 7 wt %, particularly 4 to 5 wt %. Alternatively or additionally, the macromolecules further encompass more preferably filamentary proteins, particularly gelatins, bovine gelatins, porcine gelatins or teleostean gelatins in a concentration from 0.3 to 1.5 wt %, particularly from 0.4 to 0.8 wt % which have a low gel strength of 150 Bloom or less, particularly 75 Bloom or less. Also, enzymatically hydrolysed collagen (collagen hydrolysate) may be employed alternatively or additionally, preferably in a concentration from 0.3 to 20 wt %, particularly from 1 to 10 wt %.

Macromolecules of these kinds, especially in the concentrations specified and with the viscosities resulting from this are exceptionally well suited to saturate the unspecific binding sites, and with a suitable flow velocity and density to thereby create conditions in which the target particles adhere especially well to the matrix.

In the method according to the present invention, each buffer solution mentioned as suitable in the description and in particular each buffer solution described in the sub-claims to the apparatus may be used as the buffer solution.

The matrix and a separation column surrounding it are preferably equilibrated in this arrangement before the through flow of the suspension by pre-incubation with clean buffer solution, i.e. a buffer solution containing no biological material and indeed over a sufficiently long period of time to saturate unspecific binding sites in the matrix, particularly over a duration of 3 to 20 minutes or 5 to 10 minutes. The matrix is kept continuously covered by buffer solution during equilibration. In even more preferred manner, the suspension has a critical concentration of the biological material for the separation process, which is also dependent on the buffer solution employed. The periods of time stated suffice, in accordance with the findings of the inventors, to saturate adequately the unspecific binding sites in advance. The preparative equilibration prevents undesired particles initially attaching, on introduction of the suspension into the matrix, to the unspecific binding sites of the suspension not yet completely saturated by buffer solution. During the complete procedure, the matrix is to be kept covered, so that the unspecific binding sites are not freed and the flow conditions are kept constant, since this would impair the separation result.

For the separation of undesired biological material, the eluate (i.e., a liquid leaving the matrix) is captured preferably after the through flow, wherein, after introduction of the suspension into the matrix with a still activated magnetic field, additional clean buffer solution is flowed through the matrix until the suspension has completely left the matrix, and wherein the matrix is kept fully covered by the buffer solution during the through flow. In this case, target particles are disturbants which are to be removed and they attach in the matrix until the actually desired components of the biological material are completely washed out from the matrix. The captured eluate no longer contains the target particles attached to the matrix by magnetic force, they are separated and their concentration is considerably reduced in the eluate. In the ideal case the eluate no longer contains such target particles. Subsequently, the target particles remaining in the matrix may be separately discarded or used for other purposes, by flushing them out in a separate working step.

Alternatively for purification of desired biological material, after introduction of the suspension into the matrix, with the external magnetic field still activated, additional clean buffer is flowed through the matrix until the suspension has completely left the matrix, and subsequently, the matrix is washed out with additional clean buffer solution with the external magnetic field deactivated through spatial separation or through it being switched off and the eluate is thereby captured, with the matrix being kept covered by buffer solution during the complete procedure. In this case, the liquid leaving the matrix in the phase of the activated magnetic field contains no biological material of primary interest, this liquid can be discarded or used otherwise. Only during subsequent wash out without magnetic field does the matrix set the target particles free again, which are thus contained in the eluate then captured during subsequent wash out of the matrix in a very significantly elevated degree of purification. During this wash out, the buffer solution may be the same but also a different buffer solution than during the actual HGMS phase with activated magnetic field. In this case, the target particles are contained in the other buffer solution of the eluate, or in a mixture of both buffer solutions.

Preferably, the eluate captured is centrifuged and the procedure is preferably repeated once or several times, with the centrifuged off biological material without the liquid phase of the eluate. With the separation procedure, the biological material thus remains without the disturbing target particles to be separated. Quite on the contrary, during the purification procedure the target particles remain in pure form without the buffer solution of the suspension. Insofar as the usually high degree of separation or purification already achieved after one flow through is not sufficient, the procedure can be performed again. This applies especially then when the matrix was overloaded during a separation process, otherwise only clearly decreased improvements are to be expected compared to the first flow through.

The method according to the present invention can be developed further with similar characteristics as is set out in the subclaims following the independent claims, by way of example but not exhaustively, and has similar advantages at the same time.

The invention will be described in the following with regard to further features and advantages and with reference to embodiments by way of example, and with reference to the drawings.

FIG. 1 shows a schematic front view of an embodiment of the purification apparatus according to the present invention. The purification device includes a separation column 1, a liquid storage container 11, from which buffer solution can be supplied to the separation column 1, a permanent magnet or electromagnet 7 for the generation of a strong magnetic field, and a special buffer solution, which is described in further detail elsewhere herein.

The separation column 1 has a casing and a matrix 2 arranged in it. The casing consists of non magnetic material and possesses at least one liquid inlet 6 and at least one liquid outlet 3. The liquid outlet 3 is equipped with a device 4 for influencing the flow velocity of the buffer solution in the separation column 1, which has a multi-way tap 4 and a through flow limitation device 5. Alternatively, other known devices for the regulation of the flow velocity in the separation column can be employed.

The matrix 2 is designed so that in the inside of the separation column 1, a high magnetic gradient is generated by the externally arranged magnetic field, as it is required for HGM separation. The matrix 2 has ferromagnetic material, for example stainless, magnetic stainless steel or other, which is ordered or non-ordered, filamentary, spherical or shaped differently. Examples for the design of the matrix 2 are named further below in the connection with experimental purifications.

The separation column 1 with the matrix 2 contained in it is located in a strong, preferably homogenous magnetic field, which can be created by the permanent magnet or electro magnet 7. The magnetic field can be switched on or off, for example by removal of the separation column from the field of the permanent magnet, or by switching off the electromagnet 7.

The liquid storage container 11 has a liquid inlet area 12, a reservoir area and a liquid outlet 10, from which the buffer solution can be brought into the liquid inlet 6 of the separation column 1. The liquid outlet 10 of the liquid storage container 11 is equipped with a device for influencing the outflow velocity of the liquid contained in it, which has a one-way tap 8 and a flow limitation device 9. As with the liquid outlet 3 of the separation column 1, other known devices for the regulation of the outlet flow velocity from the liquid storage container 11 can be considered here, too. Also, depending on requirements, one or multi-way taps can be used and/or interchanged.

The buffer solution mentioned above and employed according to the present invention serves for the equilibration of the separation column 1 and the suspension of the biological material to be separated. This buffer solution can contain pure water and one or several different kinds of macromolecules, which in sufficient concentration have the property to be able to saturate unspecific binding sites in the separation column 1 and of the matrix 2 contained therein. Furthermore, the buffer solution preferably has a density which is sufficiently similar to the density of the particles to be separated to strongly or possibly even completely reduce the effects of gravity on the particles and therefore, keep them in suspension. In this way a sedimentation of the particles to be separated is avoided during slow flow velocities in the separating columns. Furthermore, the buffer solution possesses a viscosity which leads to a flow velocity with laminar flow properties in the separation column 1 suitable for the separation process. Lastly, different ions may be contained in the buffer solution, as for example, but not exclusively, cations such as sodium, potassium, magnesium and calcium, or anions such as chloride, phosphate, sulfate and carbonate. Here the stated listing is by no means intended to exclude further other cations or anions.

The macromolecules employed in the buffer solution should be sufficiently large to be able to effectively saturate unspecific binding sites, but not so large that they increase the viscosity of the buffer solution critically in the concentrations to be employed. Therefore, macromolecules are preferred with a molecular weight from 10,000 to 100,000 kDa, even more preferred with a molecular weight from 30,000 to 70,000 kDa. Advantageously, the macromolecules added carry a charge which corresponds to the charge of the particles to be separated, since this preferably relates to a competitive inhibition of the unspecific binding of particles to be separated and of macromolecules to the material of the matrix 2. For example, macromolecules with a negative charge are preferably chosen if the particles to be separated are cells of which the cell wall mostly carries negative charges.

Such positively or negatively charged macromolecules are known under the heading polyelectrolytes. A subgroup of the polyelectrolytes is furthermore known under the name polyampholytes. This denominates polyelectrolytes which carry both positive and negative functional groups. The net charge of the polyampholytes can be deducted easily when knowing their isoelectric point and the pH of the buffer solution surrounding the molecule. If the pH of the buffer solution lies below the isoelectric point of the polyampholyte, its net charge lies in the positive region. With a pH value of the buffer solution above the isoelectric point, it is the other way round, so the net charge lies in the negative region. If the pH value of the buffer solution lies at or very close to the isoelectric point of the polyampholyte, it is neutral, so it carries no net charge.

Polyelectrolytes which have proved to be especially advantageous within the context of the present invention for separation of cellular material are, for example, macromolecules of the group of proteins. The group of proteins is divided into the two subgroups of the globular proteins (spherical) and the filamentary proteins (fibre-like). The conceptual division between the two named subgroups, however, is strictly speaking to be seen as diffuse, because intermediate forms between globular and filamentary proteins exist. Therefore, in the following, the terms "globular" and "filamentary" shall encompass proteins of both subgroups and transition forms.

Now, globular and filamentary proteins dissolved in liquids possess the property to bind reversibly and non-reversibly to solid surfaces, this phenomenon is mostly termed adsorption or adhesion. In the context of binding to stainless steel surfaces, scientific publications point out that on contact of proteins dissolved in liquid with stainless steel surfaces deposition of a monolayer (a single layer of molecules) of protein molecules on the stainless steel surface arises (Nakanishi et al., Journal of Bioscience and Bioengineering, 91, 2001:233-244; Fukuzaki et al., Journal of Fermentation and Bioengineering, 80, 1995:6-11). While the thickness of this monolayer lies in the range of the hydrodynamic diameter (Stokes-radius) of the respective protein molecule, so being in the range of a few nanometers, the exact areal symmetry of the monolayer has not been known until now. It can be supposed, however, that the monolayer is not shaped entirely regular. Pradier et al. point out that possibly even gaps exist between the deposited protein molecules, i.e. the stainless steel surface could not be fully covered with protein molecules (Surface and Interface Analysis, 34, 2002:50-54). Further examinations leave it unclear whether the formation of such a monolayer influences corrosion of the stainless steel surface positively or negatively (Omanovic and Roscoe, Langmuir, 15, 1999: 8315-8321, Hansen et al., Corrosion Science, 37, 1995: 1423-1441). Altogether it has to be supposed that water molecules and dissolved ions by no means are completely excluded by the monolayer.

Nevertheless, within the context of the present invention, it was found that the formation of such a monolayer is able to prevent unspecific binding of non-target particles to the matrix of a HGMS-separator extremely effectively; moreover, neither a physical nor a chemical damaging of the biological material to be separated was observed.

In the following, some proteins shall be addressed further which especially proved to be of value in the context of the present invention, without limiting the invention to these especially appropriate proteins.

At this point, the albumins, such as for example bovine or human serum albumin, should particularly preferably be named as representatives of the subgroup of the globular proteins. From the group of the albumins serum albumins of any other species, and also other albumins, such as, but not exclusively, ovoalbumin, lactoalbumin or plant albumins, can also be used, but are less preferred.

For bovine or human serum albumin in phosphate buffered isoosmolar (physiological) saline solution concentrations from 3% to 7% even more preferred from 4% to 5% were found to be optimal in the context of the present invention for the separation process for cellular material.

Distinctly lower concentrations (0.1%-1%), such as are usually added to physiologic buffers in cell research, did not lead to the desired results in the context of the present invention. On the one hand, this is explained in that such relatively low albumin concentrations are not able to efficiently saturate unspecific binding sites of the separation column 1 with non-coated matrix 2 employed in this invention. On the other hand, these low albumin concentrations do not confer the necessary density to the buffer solution, which is able to keep the particles to be separated in suspension and to prevent a gravity induced sedimentation, with slow flow velocities as well.

From the subgroup of the filamentary proteins the gelatins are to be named as particularly preferred in the context of the present invention. Due to their favorable isoelectric point of about pH 4.5 to pH 5.6 and therefore, their negative charge in the neutral pH range gelatins of class B (bovine gelatins) are found to be particularly preferred within the gelatins for separations of cellular material in the physiological pH range. A concentration range which is particularly favorable for the separation process of cellular material was found for bovine gelatins from 0.3% to 1.5%, even more preferred from 0.4% to 0.8%. Other gelatins such as gelatins of class A (porcine gelatins) or teleosteangelatins (fish gelatins), or any other gelatin and the enzymatically hydrolysed collagens (collagen-hydrolysates) as another subgroup of the gelatins are equally usable but are less preferred due to their less favorable isoelectric points, at least for separations in the physiological pH range. Generally, among the different gelatins B and the gelatins of the other groups named those are to be preferred which have a low gel strength (bloom strength), preferably less than 150 Bloom and even more preferred less than 75 Bloom.

Further macromolecules from the group of proteins, which can be employed within the context of the present invention are, in a non-exclusive listing, among others, further globular proteins, as for example β-lactoglobulin or κ-casein, or other globular proteins from the subgroups of the histones or protamines, of the globulines, the prolamines and the glutelins, as well as further filamentary proteins.

In further embodiments of the invention, the employment of other macromolecules from the group of the organic or synthetic polyelectrolytes is conceivable, for example of the synthetic polyelectrolyte Orotan 1850™ (Rohm and Haas, Philadelphia, Pa., USA) or of the organic polyelectrolyte D-glucoronic acid.

Some of the macromolecules mentioned which can be added to the buffer solution to decrease the unspecific binding of the biological material to be separated to the matrix material lead, in combination with particular buffer solutions, to an aggregation of the to be separated biological material in suspension. The aggregation affinity of red blood cells in suspension correlates positively with the molecular weight and the concentration of the added macromolecules, as well as with the ionic strength of the buffer solution. The ionic strength is understood as the total charge concentration of the dissolved ions in the buffer solution. Low ionic strengths can act against an aggregation, which is caused by added macromolecules and are even able to completely prevent it. The consideration of the hydrodynamic diameter (Stokes-radius), which can be deduced from the molecular weight and the measurement of the intrinsic viscosity enables, even more exactly than the sole consideration of the molecular weight of a particular macromolecule, the prediction of its aggregation promoting action on a suspension of red blood cells (compare the works of Jan and Chien (Journal of General Physiology, 61, 1973:638-654, 655-668) and Armstrong et al. (Biophysical Journal, 87, 2004:4259-4270)). In the following, the term "molecular weight" of a macromolecule shall always be representative for the hydrodynamic diameter (Stokes-radius) of this macromolecule, which can be deduced from it.

Within the context of the invention, it proves to be advantageous to exploit these findings and to adapt the ionic strength of the buffer solution to effectively prevent an aggregation of the biological material to be separated. For example, the inventors observed an aggregation of blood cells particularly upon suspension in gelatin containing physiological phosphate buffered saline solution. To prevent this aggregation for the separation of blood cells while using gelatins, it proved to be particularly advantageous to partly or completely replace physiological phosphate buffered saline solution with physiological phosphate buffered sucrose solution.

From the interrelationship described between particle aggregation and the special properties of the buffer solution (particularly the concentration and the molecular weight of the macromolecules, as well as the ionic strength of the buffer solution), predictions can be made, as to which combination of macromolecules and buffer solutions are particularly suitable for the separation of a specific biological material to be separated, and a macromolecule containing buffer solution can be chosen, of which the physical-chemical properties are matched to the separation conditions necessary for a specific particle. Here, the term physical-chemical properties of a buffer solution in the context of the present invention shall encompass viscosity, density, ionic strength, osmolarity, and pH value of the liquid, furthermore the kind, molecular weight, charge and concentration of the macromolecules dissolved in it and other manipulatable physical-chemical parameters of both the macromolecules as well as the liquid surrounding these.

In the following, the purification method according to the present invention will be explained in more detail stepwise.

In a first step, the separation column 1 is equilibrated with buffer solution for the saturation of unspecific binding sites. Here, the equilibration occurs by pre-incubation of the separation column 1 with a buffer solution as described above, suitable for the separation process of the specific particle suspension to be investigated, called buffer solution A in the following, over a sufficiently long time period, which is based on the macromolecules employed in the buffer solution. As a rule, this period of time measures 3 to 20 minutes, even more regularly 5 to 10 minutes, in rare cases shorter or longer periods of time can, however, also be necessary.

After equilibration the biological material to be separated is suspended in buffer solution A and is fed in to the inlet area 6 of the separation column 1, with the separation column 1 being located in the homogenous magnetic field of the horseshoe magnet or electromagnet 7. At the same time, the liquid outlet 3 of the separation column 1 is opened with the help of the multi-way tap 4. Here attention has to be taken to keep the matrix 2 always covered with buffer solution. The biological material flows through the separation column 1 and the intrinsically magnetic or the target particles previously labeled with synthetically paramagnetic particles adhere to the matrix 2. All non magnetic particles, however, pass through the separation column 1 unhindered and exit at the liquid outlet 3.

After complete addition of the biological material to be separated, the washing of the separation column 1 follows. This serves to wash out non-magnetic non-target particles remaining in the separation column 1. The liquid outlet 10 of the liquid storage container 11, containing buffer solution A, is opened with the help of the one-way tap 8, so that now pure buffer solution A flows as a washing solution through the separation column 1. Here again, attention has to be paid to keeping the matrix 2 always covered with buffer solution. The amount of the buffer solution A necessary for adequate washing for a separating column 1 with a volume of 3 ml is approximately 30-60 ml, for separating columns of other sizes it must be correspondingly adapted.

After completion of washing of the separation column 1, the liquid outlet 3 of the separation column 1 and of the liquid storage container 11 is closed. The separation column 1 is removed from the magnetic field of the horseshoe magnet 7, or the magnetic field is switched off in case of the employment of an electromagnet 7. Without the influence of the magnetic field, the target particles now release themselves from the matrix 2 and can be washed out by anterograde or retrograde washing of the separation column 1 with buffer solution A or, since the separation has now been carried out, with any other desired buffer solution.

This method is suitable both for purification of target particles because they are contained in the eluate, which was obtained by washing out of the column, as well as for the removal of target particles from the biological material to be separated. In the second case, the washing solution exiting from the separation column 1 is of interest which contains the biological material reduced by the target particles. Then, the washing solution is captured during the introduction of the biological material suspended in buffer solution A into the separation column 1 and during the subsequent washing of the separation column 1 with pure buffer solution A. Here it is important to take care that the matrix 2 is not overloaded with a number of target particles which is too high, because upon exhaustion of the capacity of the matrix 2, non-bound target particles can leave the liquid outlet 3 of the separation column 1 with the leftover biological material to be separated.

The method can be repeated with the obtained, purified target particles, in case an even higher purification should be achieved. The same applies for the washing solution captured after the flow through of the separation column 1, in case an even purer removal of target particles from the biological material to be separated is aimed for. This, however, mostly is not necessary any more because of the high degree of purification according to the present invention.

The following test examples are intended to illustrate the invention further, but without limiting the applicability to the test examples by this.

Example 1

Purification of red blood cells infected with malaria pathogens (plasmodia) from a *P. falciparum* culture with isoosmolar gelatin-containing phosphate buffered sucrose solution.

Material: Buffer solution A: isoosmolar phosphate buffered sucrose solution with 0.75% gelatin; Stainless steel wool 1 g; One-way tap; Three-way tap; 20G injection needle; 3 ml disposable syringe; 10 ml disposable syringe; 50 ml disposable syringe; and 1 neodymium horseshoe magnet.

a) Preparation of the Purification Kit
Manufacture of the Separation Column

A 3 ml disposable syringe as separation column 1 was filled to two-thirds of its total volume with one gram of stainless steel wool as matrix 2. Here care was taken that the majority of the stainless steel wool fibers came to lie in the longitudinal direction of the syringe body. A three-way tap 4 and the 20G injection needle as flow limitation device 5 were connected to the liquid outlet 3 of the syringe body. The upper third of the disposable syringe not filled with stainless steel wool served as the inlet region 6 of the separation column 1.

Equilibration of the Separation Column

The separation column so manufactured was filled retrogradely with buffer solution in vertical position through the three-way tap 4. Air bubbles were evacuated by tapping with the finger as completely as possible, it was found, however, that remaining smaller air bubbles do not influence the separation process negatively. Now, the separation column 1 was positioned between the poles of the horseshoe magnet 7, so that the complete matrix 2 was exposed to the magnetic field and equilibrated for 10 minutes.

Assembly and Positioning of the Liquid Storage Container

A one-way tap 8 equipped with an 18G needle as flow limitation device 9 was fitted to the liquid outlet 10 of the 50 ml disposable syringe which served as liquid storage container 11. This was then positioned over the separation column 1 so that the liquid exiting from the needle could drip into the inlet area of the separation column 1.

b) Preparation and Carrying Oat of the Separation Process
Preparation of the *P. falciparum* Culture for Purification of Red Blood Cells Infected with Malaria Pathogens 50 µl of red blood cells of a *P. falciparum* culture with a parasitemia of 13.51% were resuspended in 450 µl RPMI medium and oxygenated for 10 minutes under the influence of room air. The culture was then centrifuged and resuspended in 5 ml buffer solution $A_1$.

Carrying Out of the Separation Process

After completion of the 10 minute equilibration of the separation column 1, its liquid outlet 3 was opened and at the same time the resuspended cells were slowly introduced into the inlet area of the separation column 1 so that the matrix 2 remained covered with liquid permanently. After complete addition of the resuspended culture, the liquid outlet 10 of the liquid storage container 11, which contained 45 ml buffer solution $A_1$ was opened. Here a change of the flow velocity in the separation column 1 by manipulation of the liquid outlet 3 of the separation column 1 was to be avoided, and attention to be paid to keeping the matrix 2 of the separation column 1 always covered with buffer solution $A_1$. After completed addition of the buffer solution $A_1$ from the liquid storage container 11, the flow in the separation column 1 was stopped by closing of the liquid outlet 3 and the separation column 1 was removed from the magnetic field. A 10 ml disposable syringe, which is filled with buffer solution $A_1$, was attached to the three-way tap 4 and the separation column 1 washed out retrogradely. Here the eluate was captured in a suitable container and the suspension centrifuged for 5 min at 1500 g. The supernatant was discarded and the pellet resuspended in 300 µl phosphate buffered saline solution.

c) Analysis and Result

Figure 2A:
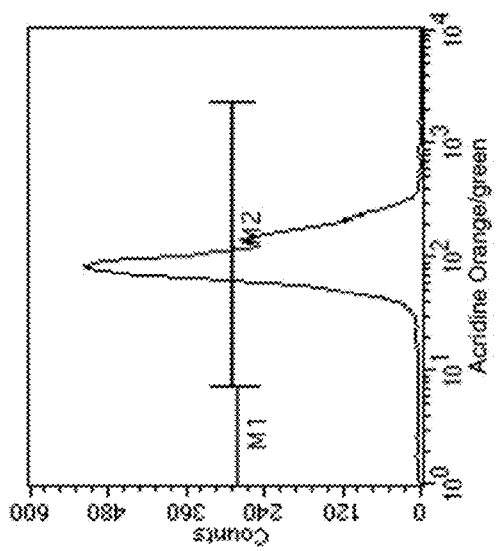
FIG. 2A shows a flow cytometric analysis of a first example of a purification according to the present invention, employing an isoosmolar phosphate buffered sucrose solution with 0.75% gelatin as buffer solution. The histogram illustrates a *P. falciparum* culture before passage through the HGMS column.
Figure 2B:
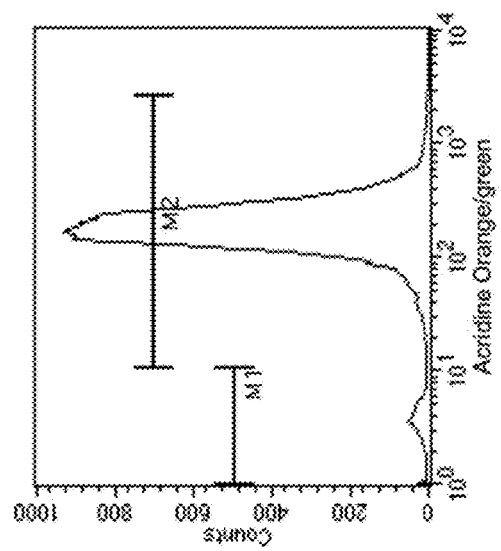
FIG. 2B shows a flow cytometric analysis of a first example of a purification according to the present invention, employing an isoosmolar phosphate buffered sucrose solution with 0.75% gelatin as buffer solution. The histogram shows the eluate after passage of *P. falciparum* culture through the HGMS column, washing the column, and removal of the separation column from the magnetic field.

Staining of the cells with acridine orange and a flow cytometric analysis as described elsewhere (Bhakdi et al., Cytometry A 2007: (71A) 662-667) then followed. FIG. 2 shows the result of the purification by means of histograms of the flow cytometric analysis. As shown in FIG. 2A, *P. falciparum* culture before passage through the high gradient magnetic separation column. M1: normal red blood cells, M2: red blood cells infected with *P. falciparum* (13.51%). As shown in FIG. 2B, eluate from the separation column 1 after passage of the culture, washing with 45 ml buffer solution $A_1$ and removal of the separation column 1 from the magnetic field. M1: normal red blood cells, M2: red blood cells infected with *P. falciparum*, purified to 99.54%. Accordingly, a blood smear stained with Giemsa showed exclusively red blood cells infected with malaria pathogens. The malaria pathogens from the purified red blood cells let themselves be cultured over several days without problems.

Example 2

Purification of red blood cells infected with malaria pathogens from a *P. falciparum* culture with phosphate buffered saline solution (PBS) containing bovine serum albumin (BSA).

Material: As listed in Example 1, but buffer solution $A_1$ replaced with buffer solution $A_2$ (PBS with 5% BSA).

a) Preparation of the Purification Kit
As described in Example 1.

b) Preparation and Carrying Out of the Separation Process
Preparation of the *P. falciparum* Culture for Purification of Red Blood Cells Infected with Malaria Pathogens As described in Example 1. The parasitemia of the *P. falciparum* culture was 14.47% in this experiment. Buffer solution $A_1$ was replaced with buffer solution $A_2$.

Carrying Out of the Separation Process

As described in Example 1, with the following differences: Buffer solution $A_1$ was replaced with buffer solution $A_2$. Then centrifugation of the eluate was carried out at 800 g for 5 min.

c) Analysis and Result

Figure 3A:
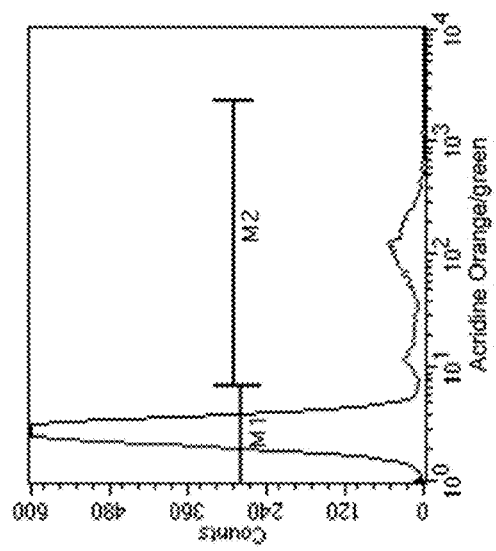
FIG. 3A shows a representation in accordance with FIG. 2A of a second example with bovine serum albumin (BSA) containing phosphate buffered saline solution (PBS) as buffer solution.
Figure 3B:
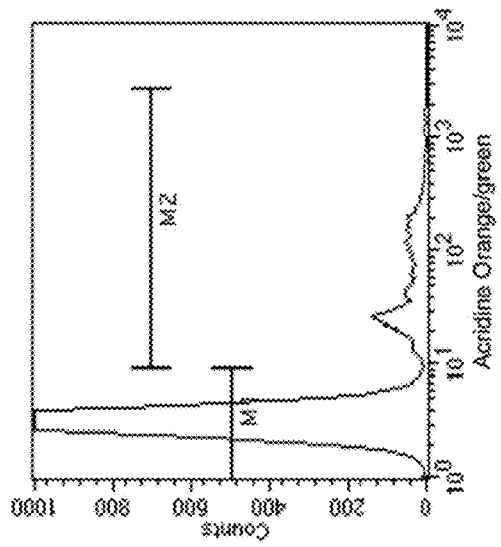
FIG. 3B show a representation in accordance with FIG. 2B of a second example with bovine serum albumin (BSA) containing phosphate buffered saline solution (PBS) as buffer solution.

The analysis was carried out analogously to Example 1. FIG. 3 shows the result of the purification by means of histograms of the flow cytometric analysis. As shown in FIG. 3A, *P. falciparum* culture before passage through the high gradient magnetic separation column. M1: normal red blood cells, M2: red blood cells infected with *P. falciparum* (14.47%). B) Eluate from the separation column 1 after passage of the culture, washing with 45 ml buffer solution $A_2$ and removal of the separation column 1 from the magnetic field. M1: normal red blood cells, M2: red blood cells infected with *P. falciparum*, purified to 97.03%. Accordingly a blood smear stained with Giemsa showed almost exclusively red blood cells infected with malaria pathogens. The malaria pathogens in the purified red blood cells were cultured further over several days without problems.

Example 3

Purification of white blood cells which carry the surface antigen CD8 (CD8 positive cells) from a suspension of white blood cells (peripheral mononuclear blood cells (PBMCs).
Material: As listed in Example 1.
a) Preparation of the Purification Kit
As described in Example 1.
b) Preparation and Carrying Out of the Separation Process
Labeling of CD8 Positive Cells with Antibody-Conjugated Synthetic Paramagnetic Particles (Microbeads)
$1.5 \times 10^7$ human peripheral mononuclear cells (PBMCs) were incubated with monoclonal rat anti-human CD8 IgG antibodies for 30 minutes in PBS/BSA 1% on ice. The cells were washed twice with the same buffer solution and subsequently incubated with anti rat IgG conjugated microbeads (Miltenyi Biotech GmbH, loc. cit.) for a further 10 minutes on ice. The cells were washed again twice in the same buffer solution and subsequently incubated for a further 30 minutes with fluorescence labeled antibodies (PE-anti CD8 and FITC-anti CD3, Simultest™, BD Biosciences, 2350 Qume Drive, San Jose, Calif. USA 95131) on ice. Then followed again a two-fold washing of the cells with PBS/BSA 1%. The cells were then centrifuged off again and resuspended in 1.5 ml of buffer solution $A_1$.
Carrying Out of the Separation Process
As described in Example 1.
c) Analysis and Result
FIG. 4 shows the result of the purification of the CD8 positive cells from the suspension of PBMCs. FIG. 4A shows the cell population of the sample. Both upper quadrants show the CD8 positive cells (23.21%). FIG. 4B shows the eluate from the separation column 1 after passage of the PBMCs, washing with 45 ml buffer solution $A_1$ and removal of the separation column 1 from the magnetic field. Both upper quadrants show the CD8 positive cells, purified to 99.17%.

Example 4

Removal (depletion) of CD8 positive cells from a suspension of PBMCs.
Material: As listed in Example 2, but employment of a 25G injection needle as a flow limitation device instead of a 20 G injection needle.
A) Preparation of the Purification Kit
As described in Example 1.
B) Preparation and Carrying Out of the Separation Process
Labelling of CD8 Positive Cells with Antibody Conjugated Synthetic Paramagnetic Particles (Microbeads)
As described in Example 3.
Carrying Out of the Separation Process
As described in Example 2, but using 15 ml buffer solution $A_2$. For this test the liquid passing through the separation column 1 was of interest. It was captured in a suitable container, the cells were centrifuged at 800 g for 5 min and resuspended in 300 µl PBS.

c) Analysis and Result
FIG. 5 shows the result of the removal of CD8 positive cells from the suspension of PBMCs. FIG. 5A shows the cell population of the sample. Both upper quadrants show the CD8 positive cells (35.41%). FIG. 5B shows the eluate from the separation column after passage of the PBMCs, washing with 15 ml buffer solution $A_2$ and removal of the separation column 1 from the magnetic field. Both upper quadrants show the CD8 positive cells, depleted to 0.57%.

All publications mentioned above are incorporated in the present patent specification by reference.

In summary the invention is based on the idea to use a technical apparatus with consumable materials for the carrying out of a high gradient magnetic separation on biological material, also denoted as a "kit", encompassing or comprising:

a separation column containing a matrix consisting of ferromagnetic material which is suitable for the generation of a high gradient magnetic field within an external strong, homogenous magnetic field, a liquid storage container, from which buffer solution A can be brought into the inlet area of the separation column, a permanent magnet or electromagnet for the generation of a strong, homogeneous magnetic field, a buffer solution A for equilibration of the separation column and suspension of the biological material to be separated, where the buffer solution A shows at least one of the three following advantageous properties:

Buffer solution A contains macromolecules for equilibration and for suspension of the biological material to be separated, which possess the property to be able to saturate unspecific binding sites in the separation column, and/or Buffer solution A has a density, which is sufficiently similar to the density of the particles to be separated to reduce the effects of gravity on the particles as far as possible and therefore to keep these suspended in buffer solution A, and/or Said buffer solution A possesses a viscosity, which contributes to a flow velocity with laminar flow properties in the separation column, suitable for the separation process.

As used in the description and claims, the singular form "a", "an" and "the" include both singular and plural references unless the context clearly dictates otherwise. For example, the term "ferromagnetic matrix" may include, and is contemplated to include, a plurality of ferromagnetic matrices. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for purification of biological material using high gradient magnetic separation, the method comprising:
    providing a ferromagnetic matrix surrounded by a separation column,
        wherein the ferromagnetic matrix is uncoated, and
        wherein the separation column comprises an elongate body defining a lumen having an inlet and an outlet;
    applying an external magnetic field to the separation column;
    saturating unspecific binding sites in the ferromagnetic matrix by applying a buffer solution to the ferromagnetic matrix, wherein the buffer solution comprises at least one macromolecule, and wherein the at least one macromolecule comprises gelatin; and
    introducing biological material into the lumen of the separation column,
        wherein a target subset of the biological material couples to the ferromagnetic matrix when the external magnetic field is applied.

2. The method of claim 1, wherein the target subset of the biological material is one of intrinsically magnetic and magnetically labeled.

3. The method of claim 1, wherein the biological material is suspended in the buffer solution.

4. The method of claim 1, wherein applying the buffer solution introduces the biological material.

5. The method of claim 4, further comprising:
    removing the external magnetic field to allow the target subset of biological material to be removed from the ferromagnetic matrix.

6. The method of claim 5, wherein the external magnetic field is removed by one of spatial separation and turning off power to the external magnetic field.

7. The method of claim 5, further comprising:
    removing the non-target subset of the biological material by washing the ferromagnetic matrix with the buffer solution.

8. The method of claim 1, further comprising:
    continuously covering the ferromagnetic matrix with the buffer solution to maintain saturation of the unspecific binding sites.

9. The method of claim 1, wherein the biological material is one of cells, cell aggregates, or cell parts.

10. The method of claim 1, wherein applying the external magnetic field comprises applying one of a permanent magnet and an electromagnet.

11. The method of claim 1, further comprising:
    providing a storage container for coupling to the separation column, wherein the storage container introduces the buffer solution into the inlet of the separation column through an adjustable flow velocity device.

12. The method of claim 1, wherein the macromolecule constitutes 3%-7% of the buffer solution.

13. The method of claim 1, wherein the separation column further comprises an adjustable flow velocity device coupled to the outlet of the separation column.

14. The method of claim 1, wherein the ferromagnetic matrix comprises one of wire-like interlaced filaments, thread-like interlaced filaments, spherical ferromagnetic elements, a ferromagnetic metallic sheet having punched-through holes, and a ferromagnetic metallic plate having punched-through holes.

15. The method of claim 1, wherein the buffer solution has a density which matches a density of the biologic material to be purified such that the biological material is suspended in the buffer solution.

16. The method of claim 1, wherein the buffer solution has a high viscosity resulting in a laminar flow through the separation column.

17. A method for separation of a target subset of biological material from a non-target subset of biological material using high gradient magnetic separation, the method comprising:
    providing a ferromagnetic matrix surrounded by a separation column, wherein the provided ferromagnetic matrix is uncoated;
    positioning the separation column in an external magnetic field; and
    applying a buffer solution to the ferromagnetic matrix to saturate unspecific binding sites in the ferromagnetic matrix, wherein the buffer solution comprises at least one macromolecule, and wherein at least one macromolecule comprises gelatin; and
    applying biological material to the ferromagnetic matrix, wherein the target subset of the biological material couples to the ferromagnetic matrix when the external magnetic field is applied to the ferromagnetic matrix.

18. The method of claim 17, further comprising:
    incubating the ferromagnetic matrix with the buffer solution for at least three minutes to equilibrate the ferromagnetic matrix.

* * * * *